United States Patent [19]

Nagata et al.

[11] Patent Number: 5,136,086

[45] Date of Patent: Aug. 4, 1992

[54] PREPARATION PROCESS OF ALIPHATIC ISOCYANATE

[75] Inventors: Teruyuki Nagata; Masaru Wada; Hideki Mizuta, all of Fukuoka, Japan

[73] Assignee: Mitsui Toatsu Chemicals, Inc., Tokyo, Japan

[21] Appl. No.: 819,657

[22] Filed: Jan. 13, 1992

Related U.S. Application Data

[63] Continuation of Ser. No. 598,113, Oct. 16, 1990, abandoned.

[30] Foreign Application Priority Data

Oct. 23, 1989 [JP] Japan ................. 1-273811
Oct. 24, 1989 [JP] Japan ................. 1-275047

[51] Int. Cl.$^5$ ............................. C07C 119/04
[52] U.S. Cl. ................................. 560/347
[58] Field of Search ........................ 560/347

[56] References Cited

U.S. PATENT DOCUMENTS 3,631,198 12/1971 Horvitz ................. 560/347
4,922,005 5/1990 Ajioka et al. ........... 560/347

FOREIGN PATENT DOCUMENTS 0384463 8/1990 European Pat. Off. .
1037933 8/1966 United Kingdom ........ 560/347
1038129 8/1966 United Kingdom ........ 560/347
1050555 12/1966 United Kingdom .
1086782 10/1967 United Kingdom .

*Primary Examiner*—P. Alan Siegel
*Attorney, Agent, or Firm*—Burns, Doane, Swecker & Mathis

[57] ABSTRACT

This invention is an industrially efficient and improved process for the preparation of aliphatic polyisocyanates by using esters as the solvent for converting aliphatic polyamines to isocyanates.

4 Claims, No Drawings

PREPARATION PROCESS OF ALIPHATIC ISOCYANATE

This application is a continuation of application Ser. No. 07/598,113 filed Oct. 16, 1990 now abandoned.

BACKGROUND OF THE INVENTION

1. Field of the Invention

The present invention relates to a process for the preparation of an isocyanate, particularly a process for preparation of an aliphatic isocyanate by phosgenating a aliphatic polyamine or hydrochloride thereof.

The isocyanate obtained by the invention is a very useful compound as a raw material for polyurethane-based materials, polyurea-based materials and polyisocyaurate based materials in chemical, resin and paint industries.

2. Description of the Prior Art

Several processes for preparing aliphatic isocyanate by phosgenating aliphatic amine or a salt thereof are known; and the following processes have been proposed.

(1) A process for carrying out phosgenation of aliphatic amine or its hydrochloride at temperature of 120° to 180° C. in a weight ratio of solvent/raw material amine of 18/1 to 30/1 [British Patent 1,086,782].

(2) A process for reacting phosgene with a mixture of an aliphatic triamino compound and hexamethylenetriamine having a ratio of 95:5 to 90:10 by weight [Japanese Patent Laid-Open Publication SHO 60-233,044(1985) ].

Other processes which have been proposed include continuous high-temperature phosgenation processes [Japanese Patent Laid-Open Publication SHO 55-88,451(1980) ], increased pressure phosgenation processes [U.S.P 2,642,449] and vapor phase phosgenation processes [Japanese Patent Laid-Open Publication SHO 63-280,050(1988)].

Processes to prepare isocyanates by reacting primary amines with phosgene in an inert solvent have been known. When the primary amines are an aromatic amine, the aromatic amine can be converted with comparative ease to a high-purity aromatic isocyanate by passing phosgene gas through a suspension of free base or hydrochloride of the aromatic amine in the solvent. In the case of aliphatic amines, however, the reaction with phosgene is generally slow compared with the reaction of an aromatic amine with phosgene, and forms, as is well known in the art, chloroderivatives as by-products due to a deamination reaction.

The chlorinated impurity is usually formed in an amount of 3 to 10% by weight and can sometimes be has high as 20% by weight. Hence the yield of the desired product undergoes a corresponding decrease.

Formation of the chlorinated impurity is primarily observed in the syntheses of aliphatic isocyanates, and are typically not found in the preparation of aromatic isocyanates.

When aliphatic isocyanates containing the chlorinated impurity are used for a polyurethane-based material, the chlorinated impurity affects the reaction of the isocyanate group with active hydrogen containing compounds. That is, the chlorinated impurity inhibits the reaction, accelerates gelation of the prepolymer and further exerts an adverse effect on the properties of the resulting polyurethane resin.

No difference is generally observed between the properties of the chlorinated impurity and corresponding isocyanate except that the boiling point of the chlorinated impurity is generally from 5° to 20° C. lower than that of the corresponding isocyanate. Specific procedures are hence required for removing the impurity and separating a high-purity aliphatic isocyanate.

Consequently, the above-mentioned processes have been proposed in order to reduce the formation of impurity as much as possible in the phosgenation step. These processes of the prior art, however, have been disadvantageous in that use of a large amount of solvent leads to low volume efficiency and very poor economy, and that extensive purification equipment is required for separating the impurity from the desired isocyanate. As a result, conventional processes have been unsatisfactory in terms of industrial production.

SUMMARY OF THE INVENTION

One object of the present invention is to provide a process for the preparation of an aliphatic polyisocyanate having a low content of the chlorinated impurity by phosgenating an aliphatic polyamine or hydrochloride thereof.

Another object of the present invention is to provide a process for preparing an aliphatic polyisocyanate with good volume efficiency in the reaction.

As a result of intensive investigation in order to accomplish these objects, it has been found that selection of an ester as a reaction solvent can surprisingly provide a desired isocyanate having a very low content of the chlorinated impurity with good volume efficiency in the reaction; and also that an aliphatic polyisocyanate containing a further reduced quantity of the impurity can be prepared by using the ester as a reaction solvent and conducting phosgenation after converting the raw material amine to hydrochloride with hydrogen chloride gas at temperature of 100° to 160° C.

That is, one aspect of the present invention is a process for the preparation of an aliphatic polyisocyanate by reacting an aliphatic polyamine or hydrochloride thereof with phosgene in the presence of an ester as a reaction solvent.

Another aspect of the invention is a process for the preparation of an aliphatic polyisocyanate where an ester is used as a reaction solvent and phosgenation is conducted after converting the raw material amine to hydrochloride with hydrogen chloride gas at temperature of 100° to 160° C.

According to the process of the invention, an aliphatic polyisocyanate having an extremely low content of chlorinated impurity can be obtained, post treatment steps such as purification by distillation can be simplified and loss of product due to heat deterioration in the post treatment steps can be decreased. Therefore, the process of the present invention is valuable as an industrial production process.

DETAILED DESCRIPTION OF THE INVENTION

Exemplary polyamines used in the present invention include straight chain aliphatic diamines such as pentamethylenediamine, hexamethylenediamine, heptamethylenediamine, octamethylenediamine, nonamethylenediamine and decamethylenediamine; branched chain aliphatic polyamine such as 2,2'-dimethyl-1,3-propanediamine, 2-methyl-1,5-pentanediamine, 2,5-dimethyl-2,5-hexanediamine and 4-aminomethyloctane-1,8-diamine; and amino-acid based polyamines such as lysine methyl ester, lysine aminoethyl ester and cystine dimethyl ester.

The reaction solvent used in the process of this invention is an esters. Various kinds of esters can be used, and fatty acid alkyl esters and aromatic carboxylic acid esters are preferred. Exemplary fatty acid alky esters include amyl formate, n-butyl acetate, isobutyl acetate, n-amyl acetate, isoamyl acetate, methylisoamyl acetate, methoxybutyl acetate, sec-hexyl acetate, 2-ethylbutyl acetate, 2-ethylhexyl acetate, cyclohexyl acetate, methylcyclohexyl acetate, benzyl acetate, ethyl propionate, n-butyl propionate, isoamyl propionate, ethyl acetate, butyl stearate, butyl lactate and amyl lactate. Aromatic carboxylic acid esters include, for example, methyl salicylate, dimethyl phthalate and methyl benzoate. More preferred esters are aliphatic esters having a boiling point of 120° to 170° C. under the atmosphoric pressure. The use of these esters is preferred in view of preventing the decomposition of isocyanates due to over-heating. These solvents can be used singly or in combination.

The amount of the solvent used in the process of this invention is preferably at a weight ratio of solvent/raw material amine in the range of 8/1 to 16/1.

When the weight ratio is less than 8/1, a large amount of amine hydrochloride is deposited and the reaction mixture becomes difficult to stir. On the other hand, a weight ratio exceeding 16/1 has little effect on the acceleration of the reaction rate and requires a larger amount of the solvent. Hence thermal efficiency in the concentration step is reduced and volume efficiency becomes industrially unfavorable.

In order to react the above aliphatic polyamine in the ester solvent mentioned above, excessive phosgene corresponding to 2 to 10 times the mole of amino group is blown through a liquid suspending the aliphatic polyamine in the ester solvent. At first phosgenation is carried out at about 0° C., aging for some time, and then phosgenation is conducted at temperature of 100° to 170° C. Alternatively, hydrogen chloride is blown through the liquid suspending the aliphatic polyamine in the ester solvent to convert the aliphatic polyamine to hydrochloride thereof, more preferably to convert the aliphatic polyamine to hydrochloride thereof in a temperature range of 100° to 160° C. Then, an excessive amount of phosgene corresponding to 2 to 10 times the mole of amino groups is blown through the liquid to conduct phosgenation at temperature of 100° to 170° C.

In the process for reacting phosgene after converting the aliphatic polyamine to the hydrochloride thereof with hydrogen chloride gas, no particular limitation is imposed on the temperature for converting the aliphatic polyamine to the hydrochloride thereof. Particularly preferred temperatures are in the range of 100° to 160° C. In order to obtain aliphatic polyisocyanate having an exteremely low content of the chlorinated impurity, the temperature for preparing the aliphatic polyamine hydrochloride is preferably in the above-mentioned range. When the temperature is lower than 100° C., the amount of chlorinated impurity formed as a by-product is liable to increase. Although the hydrochloride is prepared at temperature exceeding 160° C., further improvement in the inhibiting effect for the chlorinated impurity cannot be found and additionally, hydrochloride preparation under the conditions of strong acidity by hydrochloric acid and high temperature is not practical because problems in the reactor material can occur. The excellent results obtained in the temperature range of 100° to 160° C. is assumed to be dependent upon the solubility and particle size of the aliphatic polyamine hydrochloride.

In addition, the phosgenation process of the aliphatic polyamine hydrochloride may be carried out by using a suspension prepared by suspending separately the aliphatic polyamine hydrochloride in esters and conducting phosgenation at a at temperature of 100° to 170° C.

The phosgenation process of aliphatic polyamine hydrochloride obtained by using hydrogen chloride gas in the temperature range of 100° to 160° C., an inhibiting effect on the chlorinated impurity can be found by using the esters as a solvent.

The amount of phosgene used is the same as in the case of conventional phosgenation of amine compounds; i.e., an excessive amount of 2 to 10 times the mole of amino group. Preferred phosgenation temperatures are in the range of 100° to 170° C. Since thermal stability of aliphatic isocyanate is generally poor at high temperatures, phosgenation for a long period of time tends to cause deterioration of formed isocyanate, an increase in tar content and a reduction of yield. On the other hand, when the reaction temperature is too low, the reaction rate is very low and not practical, even though the reaction proceeds.

The process of the invention can be carried out under atmospheric pressure. In order to increase the reaction rate and inhibit formation of the chlorinated impurity, the process of the invention can also be conducted under increased pressure.

Typical preferred embodiments of the process of the present invention are illustrated hereinafter.

To a reaction vessel equipped with a reflux condenser, thermometer, phosgene (or hydrogen chloride gas) inlet tube and a stirrer, raw material aliphatic amine and a reaction solvent are charged. In the case of using an intact aliphatic amine as the starting material, subsequent reaction procedures are conducted by phosgenating at about 0° C., aging for some time, and then heating to a prescribed temperature to continue the phosgenation reaction. In the case of phosgenating the aliphatic amine after converting to hydrochloride, the prescribed amount of hydrogen chloride gas is blown through the aliphatic amine while maintaining the prescribed range of temperature, preferably from 100° to 160° C., and then phosgen is blown through the aliphatic amine hydrochloride thus formed to carry out phosgenation.

After completing the reaction, unreacted phosgene and hydrogen chloride are purged with nitrogen and the solvent is removed. The residue is distilled to obtain pure aliphatic isocyanate.

The present invention will hereinafter be illustrated in detail by way of examples and comparative examples.

EXAMPLE 1

To a lreaction flask equipped with a reflux condenser, thermometer, phosgene or hydrogen chloride gas inlet tube and a stirrer, 46.5 g (0.4 mole) of raw material hexamethylenediamine (hereinafter abbreviated as HDA) and 613.5 g of n-hexyl acetate as a solvent were charged.

Under stirring and cooling, 35 g of hydrogen chloride gas was blown over an hour while rising the internal temperature to 60° C. The resulting mixture was then heated to 155° C. and then phosgene was blown at a rate of 29.4 g/hr. The reaction was conducted for 15 hours while maintaining the temperature at 155° to 160° C.

After finishing the reaction, unreacted phosgene and hydrogen chloride were purged with nitrogen and solvent was removed. The residue was distilled under reduced pressure of 1 to 2 mm Hg to obtain 80.7 g of the product.

The product was hexamethylene diisocyanate (hereinafter abbreviated as HDI) containing 0.2% by weight of 6-chlorohexane diisocyanate (hereinafter abbreviated as CHI). The yield of HDI was 90.0% on the purity basis. Amount of CHI formed was 0.19% by mole of HDA.

EXAMPLE 2

HDA and n-hexyl acetate were charged to the reaction vessel by the same procedures as described in Example 1 and cooled to 5° C. Successively, phosgene was blown at a rate of 30 g/hr over 3 hours while maintaining the internal temperature at 0° to 5° C.

The rate of phosgene blowing was maintained at 29.4 g/hr and the internal temperature was raised to 155° C. Successively, the reaction was conducted for 12 hours while maintaining the internal temperature at 155° to 160° C. After finishing the reaction, the reaction mixture was post-treated as described in Example 1 to obtain 60.6 g of HDI (88.9% yield on purity basis). The content of CHI in HDI was 0.3% by weight, which corresponded to 0.82% by mole of HDA.

COMPARATIVE EXAMPLE 1

Trace of Example 10 in BP 1,086,782

To the same reaction vessel as described in Example 1, 29.0 g of HDA and 735.0 g of chlorobenzene were charged and the reaction was carried out at 125° to 126° C. Other procedures conducted in reaction and post-treatment were the same as described in Example 1. Thus 38.1 g of HDI was obtained. The yield was 87.9% on purity basis. The content of CHI was 1.1% by weight, which corresponded to 1.04% by mole of HDA.

EXAMPLE 3 AND COMPARATIVE EXAMPLES 2-4

The same procedures as described in Example 1 were carried out in the reaction and post treatment except that solvents illustrated in Table 1 were used in order to investigate the effect of solvents on the formation of CHI.

TABLE 1

| | Solvent | HDI (mol %/HDA) | CHI (mol %/HDA) |
|---|---|---|---|
| Example 3 | Cychlohexyl Acetate | 89.2 | 0.30 |
| Comp. Ex. 2 | ODCB | 75.9 | 3.35 |
| Comp. Ex. 3 | Mesitylene | 74.2 | 3.67 |
| Comp. Ex. 4 | MDI | 52.4 | 16.62 |

(Note)
ODCB: o-Dichlorobenzene
DMI: 1,3-Dimethylimidazolidinone

EXAMPLE 4 AND COMPARATIVE EXAMPLES 5-7

The same procedures as described in Example 1 and Comparative Examples 2 to 4 were carried out in the reaction and post-treatment except that 46.5 g (0.4 mole) of 2-methyl-1,5-pentanediamine (hereinafter abbreviated as MPDA) as a raw material and the reaction was carried out for 18 hours. Investigation was conducted on the effect of solvent upon the formation of chlorinated impurities, that is, 5-chloro-2-methylpentane isocyanate and 5-chloro-4-methylpentane isocyanate (hereinafter abbreviated as CMPI on the whole). The yield of 2-methylpentane diisocyanate (hereinafter abbreviated as MPDI) and the amount of CMPI formed are illustrated in Table 2.

TABLE 2

| | Solvent | MPDI (mol %/MPDA) | CMPI (mol %/MPDA) |
|---|---|---|---|
| Example 4 | n-Hexyl Acetate | 89.8 | 0.19 |
| Comp. Ex. 5 | ODCB | 77.2 | 3.17 |
| Comp. Ex. 6 | Mesitylene | 75.3 | 3.42 |
| Comp. Ex. 7 | MDI | 51.7 | 18.38 |

(Note)
ODCB: o-Dichlorobenzene
DMI: 1,3-Dimethylimidazolidinone

EXAMPLE 5

To the same reaction vessel as described in Example 1, 44.2 g (0.15 mole) of lysine β-aminoehtyl ester trihydrochloride (hereinafter abbreviated as LAET) and 618.8 of amyl acetate were charged, heated to 135° C. with stirring, introduced phosgen at a rate of 14.8 g/hr, and reacted for 15 hours at 135° to 140° C.

After finishing the reaction, post-treatment was conducted by the same procedures as described in Example 1 except that distillation under reduced pressure was conducted at 0.1 mm Hg. Thus, 34.5 g of lysineisocyanato-β-isocyanatoethyl ester (hereinafter abbreviated as LTI) was obtained. The yield was 85.5% on purity basis. The chlorinated impurity, that is, lysin isocyanate β-chloroethyl ester and 2-isocyanatoethyl-2-isocyanato-6-chlorohexanate (hereinafter abbreviated as CLI on the whole) were contained in a total amount of 0.8% by weight. The amount of CLI formed was 0.71% by mole of LAET.

COMPARATIVE EXAMPLES 8-10

The same procedures as described in Example 5 were carried out except that solvents were used as illustrated in Table 3 to investigate effect of solvent.

Results on Example 5 and Comparative Examples 8-10 are illustrated in Table 3.

TABLE 3

| | Solvent | LTI (mol %/LAET) | CLI (mol %/LAET) |
|---|---|---|---|
| Example 5 | Amyl Acetate | 85.5 | 0.71 |
| Comp. Ex. 8 | ODCB | 81.8 | 5.28 |
| Comp. Ex. 9 | Mesitylene | 78.1 | 5.69 |
| Comp. Ex. 10 | MDI | 56.4 | 19.80 |

(Note)
ODCB: o-Dichlorobenzene
DMI: 1,3-Dimethylimidazolidinone

EXAMPLE 6

To the same reactor as described in Example 1, 46.5 g (0.4 mole) of raw material hexamethylene diamine (hereinafter abbreviated as HDA) and 613.5 g of n-hexyl acetate as a solvent were charged. The mixture was heated to 100° C. with stirring and 35 g of hydrogen chloride gas was blown over an hour while maintaining the internal temperature at 135° to 140° C. Successively, phosgene was blown at a rate of 29.4 g/hour and the reaction was continued for 15 hours at a temperature of 155° to 160° C.

After finishing the reaction, unreacted phosgene and hydrogen chloride were purged with nitrogen and the solvent was removed. The residue was distilled under reduced pressure of 1-2 mm Hg to obtain 80.7 g of hexamethylene diisocyanate (hereinafter abbreviated as HDI). The yield was 90.0% an purity basis. The content of 6-chlorohexane diisocyanate (hereinafter abbreviated as CHI) was 0.1% by weight, which corresponds to 0.09 mole % of HDA.

COMPARATIVE EXAMPLES 11-12

The same procedures as described in Example 6 were carried out in the reaction and post-treatment exept that solvents and hydrochloride forming temperatures were used as illustrated in Table 4.

Results are illustrated in Table 4.

TABLE 4

| | Solvent | Hydrochloride forming temperature (°C.) | HDI (mol %/ HDA) | CHI (mol %/ HDA) |
|---|---|---|---|---|
| Example 6 | n-Hexyl Acetate | 135-140 | 90.0 | 0.09 |
| Comp. Ex. 11 | ODCB | 35-95 | 75.9 | 3.35 |
| Comp. Ex. 12 | mesitylene | 25-60 | 74.2 | 3.67 |

(Note) ODCB: o-Dichlorobenzene

EXAMPLE 7 AND COMPARATIVE EXAMPLES 13-14

The same procedures as described in Examples 6 were carried out in the reaction and post-treatment except that 46.5 g (0.4 mole) of 2-methyl-4,5-pentamediamine (hereinafter abbrayiated as MPDA) was used and the reaction was carried out for 18 hours. Investigation was carried out on the effect of solvents upon the chlorinated impurity, that is, 5-chloro-2-methylpentane isocyanate and 5-chloro-4-methylpentane isocyanate (hereinafter abbreviated CMPI on the whole). The yield of 2-methylpentane diisocyanate (hereinafter abbreviated as MPDI) and the amount of CMPI formed were illustrated in Table 5.

TABLE 5

| | Solvent | Hydrochloride forming temperature (°C.) | MPDI (mol %/ MPDA) | CMDI (mol %/ MPDA) |
|---|---|---|---|---|
| Example 7 | n-Hexyl acetate | 135-140 | 89.5 | 0.09 |
| Comp. Ex. 13 | ODCB | 35-95 | 74.7 | 3.46 |
| Comp. Ex. 14 | mesitylene | 25-60 | 75.3 | 3.42 |

(Note) ODCB: o-Dichlorobenzene

What is claimed is:

1. A process for the preparation of an aliphatic polyisocyanate comprising (i) converting a polyamine to a polyamine hydrochloride by reacting the polyamine with hydrogen chloride gas in the presence of a reaction solvent, and then (ii) reacting the aliphatic polyamine hydrochloride with phosgene, wherein an ester is used as the reaction solvent, and wherein the polyamine is converted to the polyamine hydrochloride with hydrogen chloride gas at temperature of from 100° to 160° C.

2. A process according to claim 1, wherein the ester is a fatty acid alkyl ester.

3. A process according to claim 1, wherein the amount of the solvent is in a ratio from 8/1 to 16/1 by weight of the aliphatic polyamine hydrochloride.

4. A process according to claim 1, wherein hexamethylenediamine hydrochloride is reacted with phosgene.

* * * * *